United States Patent [19]

Vincent

[11] 4,325,911
[45] Apr. 20, 1982

[54] STACK GAS ANALYZER AND THERMAL OXIDATION DEVICE THEREFOR

[75] Inventor: A. L. Vincent, Monrovia, Calif.

[73] Assignee: International Telephone and Telegraph Corporation, New York, N.Y.

[21] Appl. No.: 151,715

[22] Filed: May 20, 1980

Related U.S. Application Data

[62] Division of Ser. No. 48,475, Jun. 14, 1979, abandoned, which is a division of Ser. No. 871,195, Jan. 23, 1978, Pat. No. 4,211,748.

[51] Int. Cl.³ .................... G01N 31/16; G01N 31/12; G01N 31/06
[52] U.S. Cl. ........................................ 422/75; 422/88; 422/90; 204/195 T
[58] Field of Search ...................... 23/230 PC, 232 E; 422/75, 78, 90, 93, 88; 204/1 T, 195 T

[56] References Cited

U.S. PATENT DOCUMENTS

| 2,949,345 | 8/1960 | Clauss | 422/90 X |
| 2,953,441 | 9/1960 | Clauss | 422/90 X |
| 3,598,531 | 8/1971 | Bremanis | 23/230 PC |
| 3,853,474 | 12/1974 | Austin | 422/90 X |

Primary Examiner—Ronald Serwin
Attorney, Agent, or Firm—A. Donald Stolzy

[57] ABSTRACT

A flue gas analyzer including a probe module to condense water vapor, a sampling module, and a titration module including an $SO_2$ scrubber, a thermal oxidation device and a coulometric titrator.

5 Claims, 5 Drawing Figures

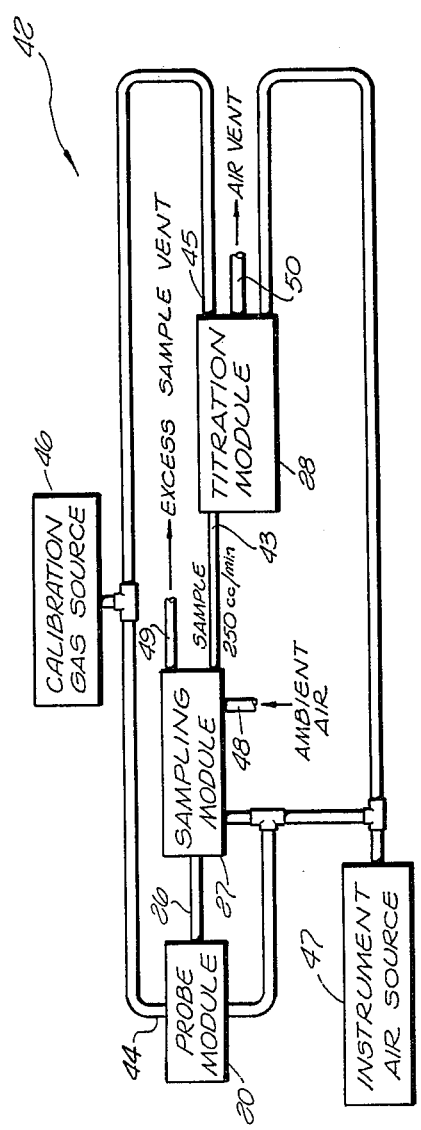
FIG. 1
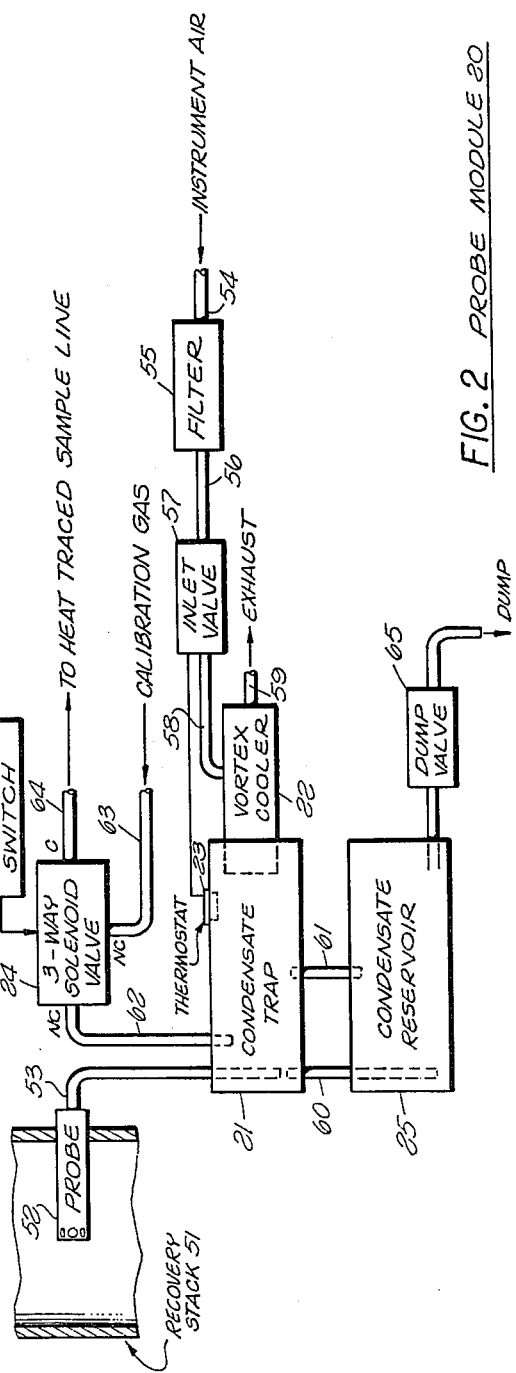
FIG. 2 PROBE MODULE 20

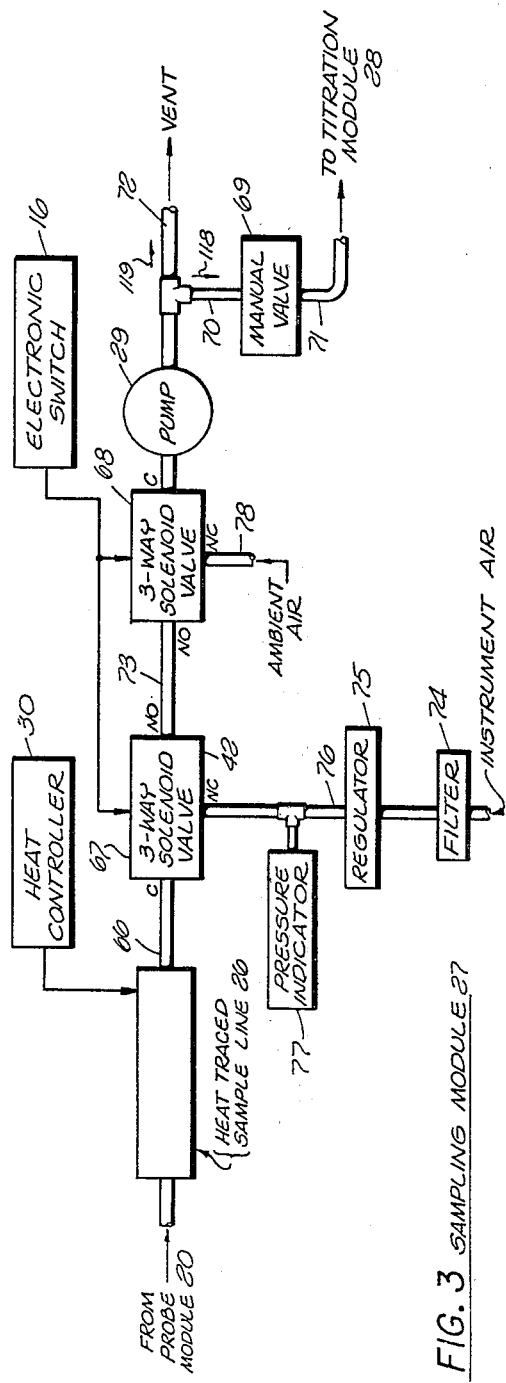
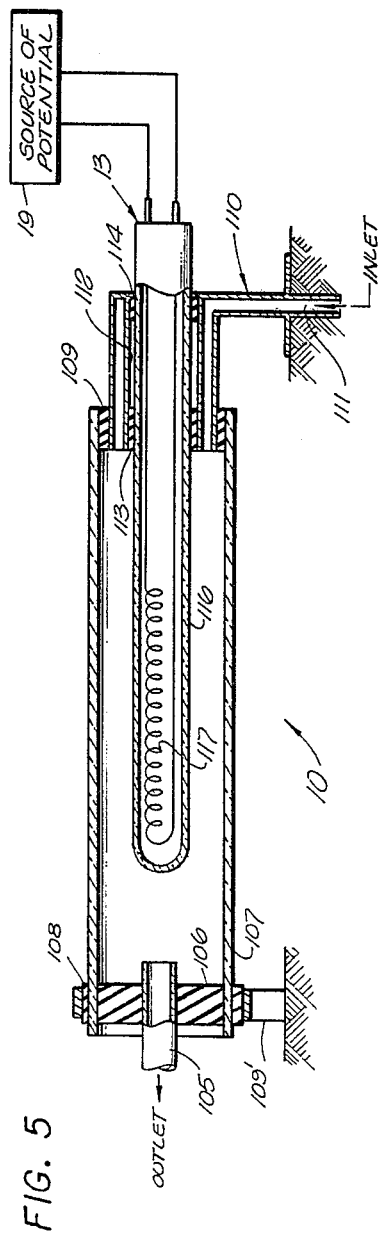
FIG. 3 SAMPLING MODULE 27
FIG. 5

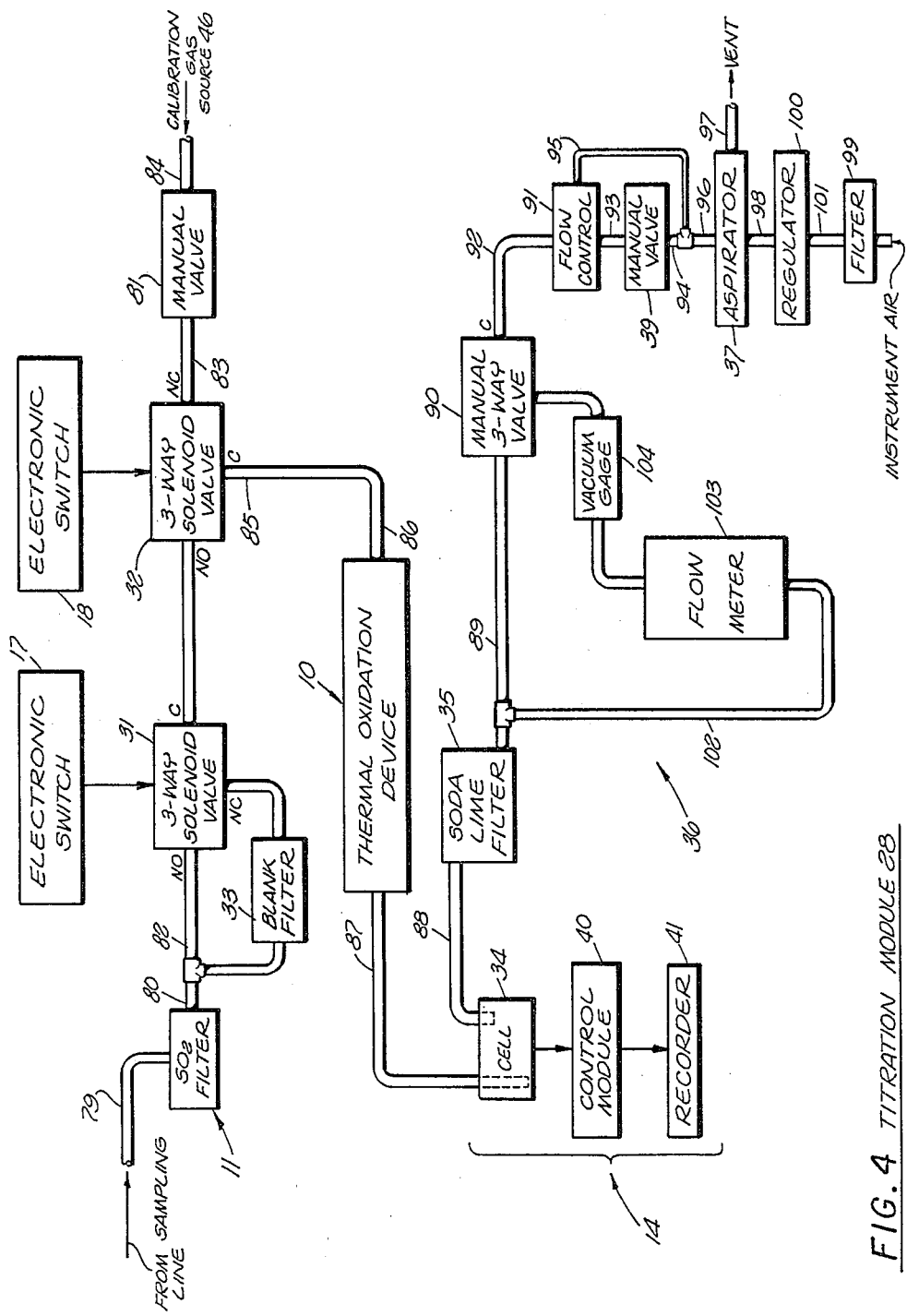
FIG. 4 TITRATION MODULE 28

STACK GAS ANALYZER AND THERMAL OXIDATION DEVICE THEREFOR

BACKGROUND OF THE INVENTION

This application is a division of copending application Ser. No. 48,475 filed June 14, 1979, and now abandoned, which, in turn, is a division of copending application Ser. No. 871,195 filed Jan. 23, 1978, now U.S. Pat. No. 4,211,748. The benefit of the filing dates of both of said copending applications is hereby claimed for this application.

This invention relates to a system for producing an output proportional to the total reduced sulfur (TRS) in flue gas including but not limited to $H_2S$, RSH, RSR and RSSR, and more particularly to a TRS stack gas analyzer having an $SO_2$ scrubber and a thermal oxidation device for the TRS to convert the same to $SO_2$ among other gases.

PRIOR ART STATEMENT

On prior art stack gas analyzer, and the present invention employs such an analyzer with a thermal oxidation device, titrates TRS without oxidizing the same. The said one analyzer is not as accurate as is desired. The titrator reacts differently with $SO_2$ and TRS; $SO_2$ has a much larger concentration than the TRS; and the titrator output is nonlinear with different $SO_2$ to TRS ratios.

Another prior art stack gas analyzer disclosed in the accompanying Du Pont Bulletin 464:

(1) Derives a first variable proportional to the sum of the $SO_2$ and TRS concentrations in a flue gas;

(2) Derives a second variable proportional to only the $SO_2$ concentration; and (3) Subtracts the second variable from the first variable to derive a third variable proportional to the TRS.

The above-numbered paragraphs describe steps which are not performed in accordance with the present invention because the present invention incorporates a scrubber to remove the $SO_2$.

The said other analyzer could not measure TRS in low ranges (e.g. 0.0–5.0 parts per million). The said other analyzer is no longer on the market because it was inaccurate. The $SO_2$ concentration is higher than that of the TRS by an order of magnitude, by two orders of magnitude, or more. It is then extremely difficult to measure accurately the difference between two variables when the difference is considerably less than each variable by itself.

SUMMARY OF THE INVENTION

According to one aspect of the present invention, there is provided a stack gas analyzer for connection from a recovery stack, said stack gas analyzer comprising: first means including an outlet for producing a flow in said first means outlet of a dehydrated mixture of the gases flowing in said recovery stack, said dehydrated mixture including sulfur dioxide, total reduced sulfur (TRS), and oxygen remaining after combustion utilizing an oxygen rate a few percent in excess of the stoichiometric rate; a scrubber having an inlet and an outlet, said scrubber inlet being connected from said first means outlet to receive said dehydrated mixture, said scrubber having a composition to remove sulfur dioxide from said dehydrated mixture without removing the said TRS, said scrubber outlet having a flow therethrough of a TRS sample mixture the same as said dehydrated mixture except for the removal of sulfur dioxide therefrom and including at least some of said oxygen; a coulometric titrator having a cell including an inlet and an outlet, and having second means to produce an electrical output signal proportional to the concentration of sulfur dioxide in an oxidized gas mixture passing through said cell from said cell inlet to said cell outlet; a conduit connected from said scrubber outlet to said cell inlet, said conduit having a flow of said TRS sample therein; and third means to heat said TRS sample in said conduit to a predetermined temperature such that said TRS is oxidized to sulfur dioxide.

According to another aspect of the present invention, there is provided a thermal device for causing reduced gas components to combine with oxygen mixed therewith, said device comprising: a non-reactive first tube; a non-reactive second tube; a heater mounted in said second tube, said first tube being longer than said heater, said heater being centrally located lengthwise and radially within said first tube, said second tube being sealed within said first tube concentrically therewith; means at each end of said first tube for sealing an inlet and an outlet thereto; and means for passing oxygen and reduced components into and out of said inlet and outlet, respectively.

According to still another aspect of the present invention, there is provided a thermal device for causing total reduced sulfur (TRS) and oxygen in a dehydrated stack gas sample to combine to form gases including sulfur dioxide, said thermal device comprising: a first tube having an internal surface and an external surface; a second tube having an internal surface and an external surface, both of said tubes being made out of materials which will not react with said TRS whether or not said TRS is oxidized; an electric heater mounted inside a portion of said second tube, said second tube portion having an external surface and being sealed within said first tube, said external surface of said second tube portion being spaced from said internal surface of said first tube to form a chamber to accommodate a heated flow of said TRS and said oxygen between said tubes; and means sealed at opposite ends of and to said first tube and forming inlet and outlet ports respectively thereat for establishing the flow of said TRS and oxygen through said chamber.

BRIEF DESCRIPTION OF THE DRAWINGS

In the accompanying drawings which illustrate exemplary embodiments of the present invention:

FIG. 1 is a block diagram of the system of the present invention;

FIG. 2 is a diagrammatic view of a probe module shown in FIG. 1, which probe module may be conventional;

FIG. 3 is a block diagram of a sampling module shown in FIG. 1, which sampling module may be conventional;

FIG. 4 is a block diagram of a titration module shown in FIG. 1, and constructed in accordance with the present invention; and FIG. 5 is a longitudinal sectional view, partly in elevation, of a thermal oxidation device shown in FIG. 4, and constructed in accordance with the present invention.

DESCRIPTION OF THE PREFERRED EMBODIMENTS

In the drawings, in FIG. 1, the system of the present invention is illustrated at 42 including a probe module 20, a sample module 27 and a titration module 28 connected in succession. Probe module 20 is connected to sampling module 27 through a heat traced sample line 26.

A conduit 43 connects sampling module 27 to titration module 28. A dehydrated sample of TRS is supplied to titration module 28 via conduit 43. This sample may be supplied at a rate of, for example, 250 cubic centimeters per minute. Probe module 20 and titration module 28 have calibration gas inlets at 44 and 45 respectively connected from a calibration gas source 46. An instrument air source 47 is connected to all three of the probe, sampling and titration modules 20, 27 and 28, respectively.

Sampling module 27 has an ambient air inlet 48 and an excess sample vent outlet 49.

Titration module 28 has an air vent outlet 50.

Probe module 20 is shown in FIG. 2. Also shown in FIG. 2 is a recovery stack 51. A perforate probe 52 is sealed through the wall of stack 51. A conduit 53 connects probe 52 to a condensate trap 21 which is refrigerated by a vortex cooler 22. Vortex cooler 22 is supplied with instrument air via a conduit 54, a filter 55, a conduit 56, an inlet valve 57 and a conduit 58. A thermostat 23 is employed to operate inlet valve 57. Vortex cooler 28 has an exhaust outlet 59. The entire refrigeration system of condensate trap 21 may be conventional. Further, all of the structures shown in FIG. 1 may be entirely conventional except titration module 28. In FIG. 2, condensate trap 21 is connected to a condensate reservoir 25 via conduits 60 and 61.

The dehydrated stack gas sample is then conducted through a conduit 62 through a three-way solenoid valve 24.

Throughout the drawings, the reference characters "NC" mean "normally closed," the reference characters "NO" mean "normally open," and "C" means "common."

An electronic switch 15 is shown in FIG. 2 for opening the inlets including conduits 62 and 63 to a common outlet 64. Only one of the inlets 62 and 63 is open at one time. Actuation of electronic switch 15 may be manual, by a clock or otherwise.

If desired, condensate reservoir 25 may be dumped every 24 hours by opening a dump valve 65 either manually, automatically by a clock, or otherwise.

Sampling module 27 is shown in FIG. 3 including the heat traced sample line 26 to which a dehydrated sample of the stack gas is supplied. Line 26 has a heat controller 30. Line 26 may be thermostatically controlled. Line 26 and heat controller 30 may be entirely conventional. Preferably, the dehydrated sample of the TRS and whatever excess oxygen exists in stack 51 is heated to approximately the temperature of the stack gas.

From line 26, the sample passes through a conduit 66, a valve 67, a valve 68 and a pump 29. The output of pump 29 is passed through an adjustable manual valve 69 having an inlet 70 and an outlet 71, outlet 71 being connected to the inlet of titration module 28. The excess of the sample from the output of pump 29 is vented at 72, or is otherwise disposed of in a conventional manner. Valves 67 and 68 are each three-way valves. They are connected together by a conduit 73. They both are operated by an electronic switch 16 as before. Valve 67 is supplied with instrument air via a filter 74 and a regulator 75. Regulator 75 has an outlet 76, the pressure of which is monitored by a pressure indicator 77. Valve 68 has an ambient air inlet 78.

Titration module 28 is shown in FIG. 4 having an inlet 79 connected to an $SO_2$ filter 11. Again, three-way solenoid valves are provided at 31 and 32 having electronic switches 17 and 18, respectively, as before. Filter 11 has an outlet 80 connected to a manual valve 81 through a conduit 82, valves 31 and 32, and a conduit 83. Manual valve 81 has an inlet 84 connected from calibration gas source 46.

A blank filter 33 is connected from filter outlet 80 to valve 31. Blank filter 33 may be a charcoal filter.

The common side of valve 32 has a conduit 85 connected to an inlet 86 of a thermal oxidation device 10. Device 10 has an outlet 87 which extends into a cell 34 of a coulometric titrator 14 having a control module 40 and a recorder 41 connected in succession therefrom. Coulometric titrator 14 may be conventional and of the type disclosed in U.S. Pat. No. 3,448,031 issued June 3, 1969.

Cell 34 has an outlet conduit 88, a soda lime filter 35, a conduit 89, a manual three-way valve 90, a flow control 91, a manual valve 39 and an aspirator 37 connected therefrom in that order. A conduit 92 connects valve 90 and flow control 91. A conduit 93 connects flow control 91 and manual valve 39. A conduit 94 connects manual valve 39 and aspirator 37. A bypass 95 is connected from flow control 91 to aspirator 37. Aspirator 37 has an outlet 96 connected to conduits 94 and 95, a vent 97, and an inlet 98 connected from a filter 99 and a regulator 100.

Filter 99 receives instrument air. A conduit 101 connects filter 99 and regulator 100. A conduit 102, a flowmeter 103 and a vacuum gage 104 are connected in succession in that order from conduit 89 to valve 90.

It is old in the art to use titration module 28 without thermal oxidation device 10. It is also old in the art to use titration module 28 with a different thermal oxidation device and without filter 11. Thus, titration module 28 may be conventional except for the construction shown in FIG. 5, and the combination of filter 11 with any thermal oxidation device.

The termal oxidation device 10 is shown in FIG. 5, most of which may be symmetrical about the axis of an outlet tube 105. Tube 105 is press fit in a polytetrafluoroethylene bushing 106. Bushing 106 is then pressed into a tube 107 made of quartz. Tube 107 is supported by rings 108 and 109 made of the same material as bushing 106. A fixed annular support 109' is pressed over ring 108. A fitting 110 is press fit in ring 109' after it has been press fit into tube 107. Fitting 110 is fixed relative to support 109'. Fitting 110 has a passage 111 in communication with the interior of tube 107 between bushing 106 and ring 109 from inlet 86 to device 10 shown in FIG. 4. Fitting 110 has a bore 112 having rings 113 and 114 pressed therein, and an electrical immersion heater (Corning 16790) 13 pressed through rings 113 and 114.

In accordance with the foregoing, except for the interior of outlet to 105, and the inlet from conduit 86, the interior of quartz tube 107 is sealed. It is sealed around heater 13. Heater 13 has a Corning "Vicor" (trademark) tube 116.

Heater 13 has an electric filament 117 which is positioned with the end of tube 116 approximately concentric with quartz tube 107 and centrally lengthwise therein.

The probe module 20 and, among other components, titrator cell 34 are purged by opening the normally closed inlets of valves 67 and 68 in FIG. 3.

Valve 24 in FIG. 2 is employed to introduce the calibration gas. The same is true for valve 32 shown in FIG. 4.

Pump 29 produces flows in conduits 70 and 72 as indicated by arrows 118 and 119, respectively, in FIG. 3.

All of the structures shown connected from conduit 89 including flowmeter 103 etc. are employed to produce a vacuum in outlet 88 of cell 34. All these structures and the combination thereof are old in the art. Aspirator 37 produces the vacuum.

Soda lime filter 35 is also conventional.

From the foregoing, it will be appreciated that probe module 20 produces an output to sampling module 27 which is a dehydrated sample of the stack gas. This dehydrated sample is again heated in line 26 in FIG. 3, and introduced to filter 11 shown in FIG. 4. Filter 11 removes the $SO_2$ from the dehydrated sample, but not the excess oxygen, and is selective. Filter 11 removes $SO_2$ to the exclusion of $H_2S$ and other TRS.

Thermal oxidation device 10 oxidizes the TRS essentially to $SO_2$ which titrator 14 is well adapted to measure.

As shown in FIG. 5, thermal oxidation device 10 employs materials at 116 and 107 which do not react to impair any TRS measurement. The material of 116 may be quartz, if desired. The peak temperature inside quartz tube 107, centrally thereof (lengthwise) may be 150° F. This temperature is adequate, but sufficiently low that, with the dimensions shown in FIG. 5, the support 109 and fitting 110 are only warm to the touch.

Preferably a source of potential 19 provides a regulated output voltage which heats element 117.

Filter 11 shown in FIG. 4 may be any conventional scrubber including but not limited to a Smith-Greenberg scrubber. However, the solution employed in scrubber 11 should be selective. That is, it should remove $SO_2$ without substantially removing the TRS and especially the $H_2S$ component thereof.

OPERATION

The present invention may be used anywhere TRS need be monitored. However, the invention may be found to have special utility in connection with monitoring TRS emissions from mill recovery boilers in the paper and pulp industry.

One of the outstanding features of the present invention is the measurement of unique, true TRS concentrations. The true TRS is derived by removing $SO_2$ through the use of scrubber 11 in FIG. 4, and by passing the TRS sample through the thermal oxidation device 10 in FIG. 4. After the $SO_2$ is removed from the flue gas, the sample passes through quartz tube 107 around concentric high temperature (e.g. 150° F.) heater 13. Source 19 may be voltage regulated, if desired. The sample in tube 107 has excess oxygen from combustion. This oxygen and the TRS in the sample are then heated and the TRS is oxidized to $SO_2$ below or far below the flashpoint, if any. Without this oxidation, the measured TRS concentrations would be ambiguous since the titrator 14 responds with different efficiencies to the various TRS compounds.

The full-scale range can be adjusted anywhere between 1 and 3000 parts per million of TRS by the use of a conventional adjustable gain amplifier (span) having a conventional zero adjustment as well.

Electronic switches 15-18 may be operated manually. Alternatively, an automatic solid state timer may be employed to control switches 15-18 which introduce zero and calibration gases. Thus, the zero and calibrate points can be automatically measured and recorded once each 24-hour period, for example.

Typically the probe module 20 may be mounted on a catwalk 80 feet above ground level on a free-standing stack. The sample is withdrawn from the stack through a Teflon tube and is immediately directed to the condensate trap 21 in what may be a refrigerated, lower portion of a NEMA 4 housing. Refrigeration is achieved by the use of the thermostat-controlled tube of the vortex cooler 22 which separates instrument air into a cold fraction and a hot fraction. The cold fraction is used for cooling. The thermostat 23 prevents over cooling. Also included in the probe housing is the solenoid valve 24 (automatically controlled, if desired) for injection of a conventional calibration gas mixture.

Associated with the probe is the condensate reservoir 25 for storage of the condensate. This reservoir can have a five gallon capacity and can be drained automatically once a day when the probe is back purged, if desired.

The heat-traced sample line 26 can conduct the sample, for example, sixty feet across the catwalk to the top of electrostatic precipitators where the sampling and titration modules 27 and 28, respectively, are located.

The sampling module 27 contains the pump 29 which may be a 1.0 cubic foot per minute pump. Pump 29 removes the sample from the stack. It also contains the controller 30 which regulates the temperature of the heat-traced line 26. The solenoid valve 24 controls the back purge of sample line and probe 52. When the instrument is in the blank or zeroing mode, the back purge is actuated and the pump 29 draws ambient air from the zero gas sample.

The sample enters the titration module 28 and is first routed through the $SO_2$ scrubber 11 where the $SO_2$ is removed in a citrate-based scrubber solution disclosed in U.S. Pat. No. 3,833,508 issued Sept. 3, 1974. Then it passes through the two, three-way solenoid valves 31 and 32, the first (valve 31) of which will divert the sample to the blank (charcoal) filter 33 if the instrument is in the blank mode. The second solenoid valve 32, when actuated, stops the sample and introduces a calibration gas into the system for calibration of the titrator cell 34. With the valves 31 and 32 not energized, the sample stream proceeds first through the thermal oxidation device 10 and then to the titrator cell 34 for analysis.

After analysis in the titrator cell 34, the sample passes first through soda lime filter 35 and then through the flow control apparatus 36. Flow through the titrator cell 34 is achieved with the air-driven aspirator 37. Prior to the aspirator there is a conventional diaphragm type flow regulator 100 which maintains a constant differential pressure across a glass and Teflon (trademark) micrometer valve 39 which is the primary flow control element. The fixed differential pressure across the orifice of the micrometer valve 39 results in a steady flow.

The control module 40 can include solid state timer and all other circuitry. The solid state timer circuitry can control automatic mode selection. The timer can have a twenty-four hour cycle which automatically selects 15-minute periods for blank measurement, system calibration and cell calibration. Each of these modes could then be separated by a 7-¾ hour measurement of TRS. In an automatic cycle, therefore, the instrument could measure blank, system calibration and cell calibration each once a day for 15 minutes.

The present invention has advantages over the gas chromatograph because of the integrated, or averaging, nature of the sampling of the invention. On the other hand, the chromatograph takes one small discrete sample every 10–15 minutes and analyzes it. This small sample is subject to wide variations in concentration because of localized turbulence in the stack. The present invention, however, continuously pulls the sample through the system and through the cell 34, resulting in an integrated or averaged sample.

During a period of six weeks of operation, the solution of cell 34 did not require changing, and the solution of scrubber 11 was changed only after three weeks of operation. At the normally low TRS concentrations, and because the cell 34 sees only $SO_2$, it is anticipated that the cell solution should require changing only every two to three months.

It is recommended that the daily maintenance schedule include checking flow rate and adjusting as necessary, checking fluid levels and checking the reading of recorder 41 to verify proper operation and values in the various modes.

In many instances, TRS monitors have been found important, not only for proof of compliance with emission standards, but also for the additional information it gives the boiler operators on the state of the smelt bed and of the fire in the boiler.

Source 19 in FIG. 5 may or may not keep the temperature about heating element 117 approximately constant, as desired.

What is claimed is:

1. Combustion apparatus comprising: a device for burning combustible material to provide a stack gas mixture including sulfur dioxide and total reduced sulfur; means to sequester a sample of said mixture; means for cooling said sample to dehydrate said mixture; means to remove the sulfur dioxide in said sample from said sample leaving a remnant including total reduced sulfur; means for reheating said remnant to cause sulfur or sulfur compounds in said remnant to be oxidized to form sulfur dioxide and means to detect the amount of sulfur dioxide whenever the same is formed by the said reheating means as aforesaid.

2. The invention as defined in claim 1, wherein said detection means includes a coulometric titrator to detect the concentration of said sulfur dioxide in said oxidized remnant.

3. The invention as defined in claim 2, wherein means are connected from said detection means to indicate the concentration of the sulfur dioxide in said oxidized remnant.

4. The invention as defined in claim 1, wherein means are connected from said detection means to indicate the concentration of the sulfur dioxide in said oxidized remnant.

5. The invention as defined in claim 1, wherein said remnant is reheated to a temperature of about 150 degrees Fahrenheit.

* * * * *